(12) United States Patent
Michaud et al.

(10) Patent No.: US 10,723,836 B2
(45) Date of Patent: Jul. 28, 2020

(54) HYDROCARBON POLYMERS COMPRISING TWO EXO-VINYLENE CYCLIC CARBONATE TERMINAL GROUPS

(71) Applicant: Bostik SA, La Plaine Saint-Denis (FR)

(72) Inventors: Guillaume Michaud, Compiegne (FR); Frédéric Simon, Pont l'Eveque (FR); Stéphane Fouquay, Mont Saint Aignan (FR)

(73) Assignee: BOSTIK SA, La Plaine Saint-Denis (FR)

(*) Notice: Subject to any disclaimer, the term of this patent is extended or adjusted under 35 U.S.C. 154(b) by 151 days.

(21) Appl. No.: 15/565,334

(22) PCT Filed: Apr. 5, 2016

(86) PCT No.: PCT/FR2016/050774
§ 371 (c)(1),
(2) Date: Oct. 9, 2017

(87) PCT Pub. No.: WO2016/162627
PCT Pub. Date: Oct. 13, 2016

(65) Prior Publication Data
US 2018/0072842 A1 Mar. 15, 2018

(30) Foreign Application Priority Data
Apr. 10, 2015 (FR) ..................... 15 53103

(51) Int. Cl.
*C08G 61/08* (2006.01)
*C07D 317/38* (2006.01)
*C08G 61/12* (2006.01)
*C08G 71/04* (2006.01)
*C08G 61/06* (2006.01)
*C08F 2/42* (2006.01)
*C08G 61/04* (2006.01)
*C08F 2/40* (2006.01)
*C08F 2/38* (2006.01)
*C08F 32/04* (2006.01)

(52) U.S. Cl.
CPC ........... *C08G 61/08* (2013.01); *C07D 317/38* (2013.01); *C08F 2/38* (2013.01); *C08F 2/40* (2013.01); *C08F 2/42* (2013.01); *C08F 32/04* (2013.01); *C08G 61/04* (2013.01); *C08G 61/06* (2013.01); *C08G 61/12* (2013.01); *C08G 71/04* (2013.01); *C08G 2261/135* (2013.01); *C08G 2261/1644* (2013.01); *C08G 2261/3322* (2013.01); *C08G 2261/3323* (2013.01); *C08G 2261/3324* (2013.01); *C08G 2261/3325* (2013.01); *C08G 2261/418* (2013.01); *C08G 2261/76* (2013.01); *C08G 2261/80* (2013.01); *C08G 2261/90* (2013.01)

(58) Field of Classification Search
CPC ........ C08G 61/08; C08G 61/06; C08G 61/04; C08G 61/12; C08G 2261/1644; C08G 2261/332; C08G 2261/3322; C08G 2261/3323; C08G 2261/3324; C08G 2261/418; C08F 2/38; C08F 2/40; C08F 2/42
See application file for complete search history.

(56) References Cited

U.S. PATENT DOCUMENTS

| 7,915,375 B2 * | 3/2011 | Pawlow ................. C08G 61/08 526/217 |
| 2013/0331532 A1 * | 12/2013 | Porta Garcia ........... C08F 24/00 526/269 |
| 2016/0215163 A1 * | 7/2016 | Hoffmann ................ C08F 8/00 |

FOREIGN PATENT DOCUMENTS

| DE | 10 98 953 | 2/1961 |
| EP | 2 851 379 | 3/2015 |
| EP | 2 851 403 | 3/2015 |
| WO | WO-2013/144299 | 10/2013 |
| WO | WO-2014/091173 | 6/2014 |
| WO | WO-2015039803 A1 * | 3/2015 ............... C08F 8/00 |

OTHER PUBLICATIONS

International Search Report dated Jun. 16, 2016 for PCT/FR2016/050774.

* cited by examiner

*Primary Examiner* — Ling Siu Choi
*Assistant Examiner* — David L Miller
(74) *Attorney, Agent, or Firm* — NK Patent Law

(57) ABSTRACT

The invention relates to a hydrocarbon polymer comprising two exo-vinylene cyclic carbonate terminal groups, of formula (1), production method thereof and use of same for the production of coating, mastic and adhesive compositions.

10 Claims, No Drawings

HYDROCARBON POLYMERS COMPRISING TWO EXO-VINYLENE CYCLIC CARBONATE TERMINAL GROUPS

CROSS-REFERENCE TO RELATED APPLICATIONS

This application is a U.S. National Stage application of International Application No. PCT/FR2016/050774, filed Apr. 5, 2016, which claims the benefit of French Application No. 1553103, filed Apr. 10, 2015.

The present invention relates to hydrocarbon-based polymers comprising two exo-vinylene cyclocarbonate end groups (also referred to as hydrocarbon-based polymers bearing exo-vinylene cyclocarbonate end groups in the present patent application).

The invention also relates to the use of these hydrocarbon-based polymers for the preparation of non-isocyanate polyurethanes, by reaction with at least one compound comprising at least one amine group. These polyurethanes, once formulated, are intended to be used in coating, mastic or adhesive compositions.

Polyurethanes are conventionally synthesized by reaction between a diol and a diisocyanate. Diisocyanates are toxic compounds as such and are generally obtained from phosgene, which is itself very toxic by inhalation or by contact. The manufacturing process used industrially generally involves the reaction of an amine with an excess of phosgene to form an isocyanate.

The search for alternatives to the synthesis of polyurethanes without using isocyanate (or NIPU for Non-Isocyanate PolyUrethane) thus represents a major challenge.

This search has formed the subject of numerous studies. The approaches most extensively studied concern the use of polymers that are capable of reacting with amines or amine oligomers to form polyurethanes.

Patent application WO 2014/091173, in the name of Bostik and the CNRS, describes hydrocarbon-based polymers comprising two end groups bearing a (2-oxo-1,3-dioxolan-4-yl) end group which may be obtained by ring-opening metathesis polymerization starting from at least one cyclic cycloolefin, at least one non-cyclic unsaturated chain-transfer agent comprising a (2-oxo-1,3-dioxolan-4-yl) end group, and at least one metathesis catalyst.

These polymers can subsequently react with a (poly) amine to form non-isocyanate polyurethanes, which may be advantageously used to formulate coating, mastic or adhesive compositions. However, this reaction is relatively lengthy and remains to be improved.

Example 4 of patent application WO 2014/091173 especially discloses the reaction of an unsaturated polyolefin comprising two (2-oxo-1,3-dioxolan-4-yl)methyloxycarbonyl end groups with a primary diamine of polyetherdiamine type, used in stoichiometric proportions, to form a polyurethane that can be formulated in the form of a two-pack adhesive composition. The duration of this reaction is 12 hours at 80° C.

In order to overcome the drawbacks disclosed in patent application WO 2014/091173, it is proposed to use novel intermediates that allow the synthesis of polyurethanes without using isocyanate, which are intended especially for the manufacture of coating, mastic or adhesive compositions.

Thus, the present invention relates to a hydrocarbon-based polymer comprising two exo-vinylene cyclocarbonate end groups, said hydrocarbon-based polymer being of formula (1) below:

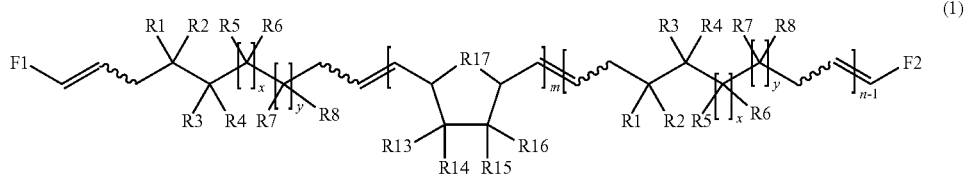

in which:
- each bond noted $\sim$ is a carbon-carbon single bond geometrically oriented on one side or the other relative to the double bond (cis or trans) to which it is bonded;
- the groups R1, R2, R3, R4, R5, R6, R7 and R8, which may be identical or different, are chosen from a hydrogen atom, a halogen atom, an alkyl group, a heteroalkyl group, an alkoxycarbonyl group or a heteroalkoxycarbonyl group;
- at least one, and preferably one, of the groups R1 to R8 possibly forming part of the same saturated or unsaturated hydrocarbon-based ring or heterocycle, with at least one other, and preferably with one other, of the groups R1 to R8, according to the valency rules of organic chemistry;
- at least one of the pairs (R1,R2), (R3,R4), (R5,R6) and (R7,R8) possibly being an oxo group;
- x and y, which may be identical or different, are integers within a range from 0 to 5, preferably from 0 to 2, and even more preferably x is equal to 1 and y is equal to 1, the sum x+y preferably being within a range from 0 to 4 and even more preferably from 0 to 2;
- the groups R13, R14, R15 and R16, which may be identical or different, are chosen from a hydrogen atom, a halogen atom, an alkyl group, a heteroalkyl group, an alkoxycarbonyl group or a heteroalkoxycarbonyl group;
- at least one of the groups R13 to R16 possibly forming part of the same saturated or unsaturated hydrocarbon-based ring or heterocycle, with at least one other of the groups R13 to R16, according to the valency rules of organic chemistry;
- the group R17 is $CH_2$, O, S, C(=O) or $NR_0$, $R_0$ being an alkyl group, preferably a linear alkyl group, comprising from 1 to 22, preferably from 1 to 14, carbon atoms; and
- n is an integer greater than or equal to 2 and m is an integer greater than or equal to 0, the mole ratio m/n being within a range from 0/100 to 90/10, preferably from 25/100 to 75/50 and more preferentially being equal to 50/50; n and m also being such that the number-average molar mass Mn of the hydrocarbon-based polymer of formula (1) is within a range from 400 to 50 000 g/mol, preferably from 600 to 20 000 g/mol, and the polydispersity (PDI) of the hydrocarbon-based polymer of formula (1) is within a range from 1.0 to 3.0, preferably from 1.0 to 2.0 and even more preferably from 1.45 to 1.85;

F1 is represented by the following formula:

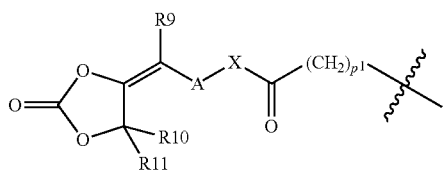

and F2 is represented by the following formula:

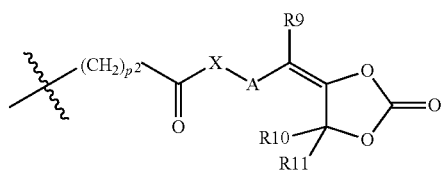

in which:

p1 and p2, which may be identical or different, each represent an integer equal to 0, 1, 2 or 3, preferably with p1=0 or p2=0 and more preferentially p1=p2=0;

X is an oxygen atom or a nitrogenous group NR12 in which R12 is a C1-C6 alkyl group;

A is a C1-C6 alkylene group;

R9 is a hydrogen atom, a C1-C6 alkyl group, a C1-C6 alkyl group oxyalkylenated with one or more C1-C6 oxyalkylene groups, a C5-C6 cycloalkyl group, a phenyl group or an alkylphenyl group with a C1-C4 alkyl chain;

R10 and R11, which may be identical or different, each represent a hydrogen atom, a C1-C6 alkyl group, a C1-C6 alkyl group oxyalkylenated with one or more C1-C6 oxyalkylene groups, a C5-C6 cycloalkyl group, a phenyl group or an alkylphenyl group with a C1-C4 alkyl chain.

Preferably, the C1-C6 alkyl group oxyalkylenated with one or more C1-C6 oxyalkylene groups as envisaged in the definition of R9, R10 and R11 previously is a C1-C4 alkyl group oxyalkylenated with one or more C1-C4 oxyalkylene groups (such as oxymethylene, oxyethylene, oxypropylene or oxybutylene).

Needless to say, all the formulae are given here in accordance with the valency rules of organic chemistry.

The main chain of the polymer of formula (1) thus comprises one or two types of repeating units, a first type of repeating unit repeated n times and a second, optional, type of repeating unit repeated m times.

As is seen above, the end groups F1 and F2 are generally symmetrical relative to the main chain, i.e. they substantially correspond, with the exception of the indices p1 and p2.

In the present patent application, unless indicated otherwise:

the term "end group" means a group located at the end of a chain (or end of the main chain) of the polymer. The polymer according to the invention comprises a main chain, i.e. a longer chain, the two ends of which are the end groups of the polymer according to the invention.

the term "exo-vinylene cyclocarbonate group" means a group F1 or F2 as described previously.

the term "alkyl group" means a linear or branched, cyclic or acyclic hydrocarbon-based (including polycyclic) compound comprising, unless otherwise indicated, generally from 1 to 22 carbon atoms. Such an alkyl group usually comprises from 1 to 14, preferably from 1 to 8, carbon atoms.

the term "heteroalkyl group" means, according to the invention, an alkyl group in which at least one of the carbon atoms is substituted with a heteroatom chosen from the group formed by O and S.

the term "alkoxycarbonyl group" means a saturated or partially unsaturated, linear or branched (monovalent) alkyl group comprising from 1 to 22, preferably from 1 to 14, carbon atoms, and also a divalent —COO— group.

the term "heteroalkoxycarbonyl group" means, according to the invention, an alkoxycarbonyl group in which at least one of the carbon atoms is substituted with a heteroatom chosen from the group formed by O and S.

the term "halogen atom" means an iodo, chloro, bromo or fluoro group, preferably a chloro group.

the term "hydrocarbon-based ring" means a saturated or unsaturated hydrocarbon-based cyclic (including polycyclic) compound which may comprise from 3 to 22 carbon atoms and optionally at least one C=O group.

the term "heterocycle" means a hydrocarbon-based ring which may comprise an atom other than carbon in the ring chain, for instance oxygen, sulfur or the group $NR_0$ as defined previously, namely an alkyl group, which is preferably linear, comprising from 1 to 22, preferably from 1 to 14, carbon atoms.

the term "at least one of the R1 to R8 groups possibly forming part of the same saturated or unsaturated hydrocarbon-based ring or heterocycle, with at least one other of the groups R1 to R8, according to the valency rules of organic chemistry" means, according to the invention, that these groups, whether or not they are borne by the same carbon, are bonded together by a hydrocarbon-based chain (which may include the carbon atoms of the main chain of the polymer of formula (1)) optionally comprising at least one C=O group and/or at least one heteroatom such as S or O, so as to form a hydrocarbon-based ring or a heterocycle, as defined above. In certain cases, these groups may denote chemical bonds. For example, when one of the groups R3 or R4 with one of the groups R5 or R6 together form, with the carbon atoms of the main chain of the polymer of formula (1) supporting them, an epoxide ring, said groups denote a bond linking the carbon atom supporting them to the oxygen atom of the epoxy group. These definitions are also applicable to the groups R13 to R16.

the term "pair (R1,R2) possibly being an oxo group" means, according to the invention, that the pair (R1,R2) is such that

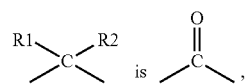

in which C is the carbon atom which supports the two groups forming the pair (R1,R2). This is also applicable to the pairs (R3,R4), (R5,R6) and (R7, R8).

The polydispersity PDI (or dispersity $Đ_M$) is defined as the ratio Mw/Mn, i.e. the ratio of the weight-average molar mass of the polymer to the number-average molar mass of said polymer.

The two average molar masses Mn and Mw are measured according to the invention by size exclusion chromatography (SEC), usually with PEG (polyethylene glycol) or PS (polystyrene) calibration, preferably PS calibration.

Preferably, the groups R5 to R8 are each a hydrogen atom.

If p1=0 or p2=0, then there is no divalent group $(CH_2)_{p1}$ or $(CH_2)_{p2}$ in formula F1 or F2 and $—(CH_2)_{p1}—$ becomes a single bond — or $—(CH_2)_{p2}—$ becomes a single bond —.

When one of the indices m, n or n−1, x or y, which applies to a set of two square brackets, is equal to zero, this means that there is no group between the square brackets to which this index applies. Thus,

means ——, and

means ═══.

Each of the double bonds of the polymer of formula (1) is geometrically cis or trans oriented, and is preferably of cis orientation. The geometrical isomers of the polymer of formula (1) are generally present in variable proportions, usually with a majority of cis (Z) and preferentially all the double bonds are of cis (Z) orientation. It is also possible according to the invention to obtain just one of the geometrical isomers, depending on the reaction conditions and in particular depending on the nature of the catalyst used.

The polymers of formula (1) according to the invention may be solid polymers or liquid polymers, at room temperature (about 23° C.).

Preferably, the polymers are liquid at 23° C., i.e. they have a viscosity ranging from 1 to 500 000 mPa·s at 23° C.

In general, the viscosity may be measured in a manner well known to those skilled in the art. In particular, the viscosity may be measured with a Brookfield viscometer, choosing the needle and the spindle speed appropriately as a function of the viscosity range to be measured.

According to one variant of the invention, when m is equal to 0, the polymer of formula (1) may be represented by formula (2) below:

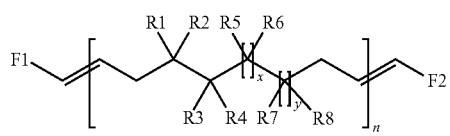

(2)

in which: x, y, n, F1, F2, R1, R2, R3, R4, R5, R6, R7 and R8 have the meanings given previously.

Formula (2) illustrates the case where the main chain of the polymer of formula (1) comprises only one type of repeating unit, repeated n times.

Particularly preferably, x is equal to 1 and y is equal to 1.

When, according to a preferred variant, m is equal to 0 and R1 to R8 denote hydrogen atoms, with at least one of the pairs (R1,R2), (R3,R4), (R5, R6) and/or (R7,R8) possibly denoting an oxo group, the polymer of formula (2) is solid at room temperature.

According to another variant of the invention, preferably:
m is other than zero
and/or
at least one of the groups R1 to R8 and/or R13 to R16 comprises an alkyl group (and thus denotes a group other than a hydrogen atom and a halogen atom)
or
at least one of the groups R1 to R8 forms part of the same saturated or unsaturated hydrocarbon-based ring or heterocycle, with at least one other of the groups R1 to R8, according to the valency rules of organic chemistry,
with
at least one of the pairs (R1,R2), (R3,R4), (R5,R6) and/or (R7,R8) possibly denoting an oxo group.

In this case, the polymer of formula (1) is liquid at room temperature.

According to a particular embodiment of the invention, F1 and F2 are identical.

According to a preferred embodiment of the invention, F1 and F2 are different.

According to a particular embodiment, X is an oxygen atom.

According to another particular embodiment, X is a group $NR_{12}$ in which $R_{12}$ is as defined previously.

Preferably:
p1 or p2=0, and more preferentially p1=p2=0,
X is an oxygen atom or a group NR12 in which R12 is a methyl group,
A is a C1-C6 alkylene group,
R9 is a hydrogen atom,
R10 and R11 are methyl groups.

The hydrocarbon-based polymers bearing exo-vinylene cyclocarbonate end groups according to the invention may form, after reaction at temperatures below 100° C. with amines or amine oligomers, an adhesive seal which has high cohesion values, in particular greater than 1.5 MPa (megapascals). Such cohesion values allow use as an adhesive, for example in the field of construction, transport or industry in general.

The ability of the hydrocarbon-based polymers bearing exo-vinylene cyclocarbonate end groups according to the invention to react more rapidly compared with those of the prior art with amines or amine oligomers at temperatures below 100° C., or even at room temperature (i.e. about 23° C.) for the liquid polymers of the invention, is thus particularly advantageous.

The hydrocarbon-based polymers bearing exo-vinylene cyclocarbonate end groups according to the invention thus make it possible to obtain an adhesive seal with satisfactory mechanical properties, more rapidly than the hydrocarbon-based polymers of the prior art mentioned previously.

The mechanical properties of the adhesive seal, and especially its cohesion values, may be measured in accordance with standard ISO 527-1 or ASTM D 638-03, and especially under the operating conditions described in Example 9 of patent application FR No. 15/50500. In this example, measurement of the breaking strength and of the elongation at break by tensile testing was performed, for each of the adhesive compositions, according to the protocol described below.

The principle of measuring the breaking strength and the elongation at break of adhesive compositions by tensile testing consists in stretching, in a tensile testing machine whose mobile jaw moves at a constant speed equal to 100 mm/minute, a standard test specimen constituted of the crosslinked adhesive composition and in recording, at the time when the test specimen breaks, the applied tensile stress (in MPa) and the elongation of the test specimen (in %).

The standard test specimen is dumbbell-shaped, as illustrated in international standard ISO 37. The narrow part of the dumbbell used has a length of 20 mm, a width of 4 mm and a thickness of 500 μm.

To prepare the dumbbell, the adhesive composition was heated to 100° C. and then extruded on an A4 sheet of silicone paper to an amount sufficient to form thereon a film 300 μm thick. The film is left for 7 days at 23° C. and 50% relative humidity to crosslink, and the dumbbell is then obtained by simply cutting it out from the crosslinked film.

The invention also relates to a process for preparing at least one hydrocarbon-based polymer comprising two exo-vinylene cyclocarbonate end groups according to the invention, said process comprising at least one step of ring-opening metathesis polymerization, in the presence:

of at least one metathesis catalyst, preferably a ruthenium-comprising catalyst, even more preferably a Grubbs catalyst, of at least one mono- or di-exo-vinylene cyclocarbonate chain-transfer agent (CTA) of formula (C1) or (C2), respectively, below:

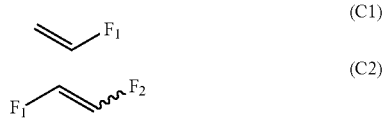

in which:
F1 and F2 are as defined previously, and
the $\sim$ bond is a carbon-carbon single bond geometrically oriented on one side or the other relative to the double bond (cis or trans) in formula (C2);
of at least one compound of formula (A) below:

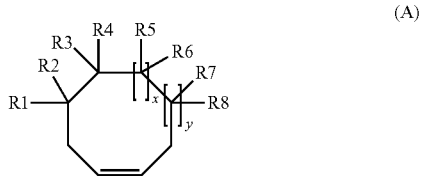

in which:
the groups R1, R2, R3, R4, R5, R6, R7 and R8, which may be identical or different, are chosen from a hydrogen atom, a halogen atom, an alkyl group, a heteroalkyl group, an alkoxycarbonyl group or a heteroalkoxycarbonyl group;
at least one of the groups R1 to R8 possibly forming part of the same saturated or unsaturated hydrocarbon-based ring or heterocycle, with at least one other of the groups R1 to R8, according to the valency rules of organic chemistry; and
at least one of the pairs (R1,R2), (R3,R4), (R5,R6) and (R7,R8) possibly being an oxo group;
x and y are integers independently within a range from 0 to 5, preferably from 0 to 2, and even more preferably x is equal to 1 and y is equal to 1, the sum x+y preferably being within a range from 0 to 4 and even more preferably from 0 to 2;
and
of optionally at least one compound of formula (B):

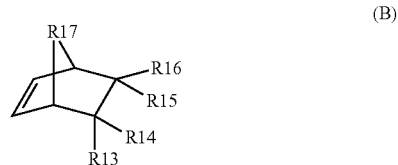

in which:
the groups R13, R14, R15 and R16, which may be identical or different, are chosen from a hydrogen atom, a halogen atom, a heteroalkyl group, an alkoxycarbonyl group and a heteroalkoxycarbonyl group;
at least one, and preferably one, of the groups R13 to R16 possibly forming part of the same saturated or unsaturated ring or heterocycle, with at least one other, and preferably with one other, of the groups R13 to R16, according to the valency rules of organic chemistry; and
the group R17 is $CH_2$, O, S, C(=O) or $NR_0$, $R_0$ being an alkyl group, preferably a linear alkyl group, comprising from 1 to 22, preferably from 1 to 14, carbon atoms;
for a reaction time ranging from 2 to 24 hours and at a temperature within a range from 20 to 60° C.

The time and the temperature for this polymerization reaction generally depend on the reaction conditions and in particular on the content of catalytic charge. A person skilled in the art is capable of adjusting them as a function of the circumstances.

The CTA is a compound which comprises one or two exo-vinylene cyclocarbonate functions.

The CTA of formula (C1) is said to be monofunctional when it comprises an exo-vinylene cyclocarbonate group.

The CTA of formula (C2) is said to be difunctional when it comprises two exo-vinylene cyclocarbonate groups, which may be identical or different.

The mole ratio of the CTA of formula (C1) to the compound of formula (A), or to the sum of the compounds of formulae (A) and (B) if the compound of formula (B) is present, is within a range from $1\times10^{-3}$ to 1.0, preferably from $1\times10^{-2}$ to 0.250.

The mole ratio of the CTA of formula (C2) to the compound of formula (A), or to the sum of the compounds of formulae (A) and (B) if the compound of formula (B) is present, is within a range from $0.5\times10^{-3}$ to 0.5, preferably from $0.5\times10^{-2}$ to 0.125.

The compounds of formula (A) generally comprise from 6 to 30, preferably from 6 to 22, carbon atoms.

The compounds of formula (B) generally comprise from 6 to 30, preferably from 6 to 22, carbon atoms.

In a preferred embodiment of the invention, x=y=1.

Ring-opening metathesis polymerization (ROMP) is a reaction that is well known to those skilled in the art. In the present patent application, this reaction is performed in the presence of a monofunctional CTA of formula (C1) or of a difunctional CTA of formula (C2).

The cyclic compounds of formula (A) are preferably, according to the invention, chosen from the group formed by cycloheptene, cyclooctene, cyclononene, cyclodecene, cycloundecene, cyclododecene, 1,5-cyclooctadiene, cyclononadiene, 1,5,9-cyclodecatriene, 5-epoxycyclooctene, 5-oxocyclooctene, and 5-alkylcyclooctenes in which the alkyl part is C1-C22 and preferably C1-C14, and mixtures thereof.

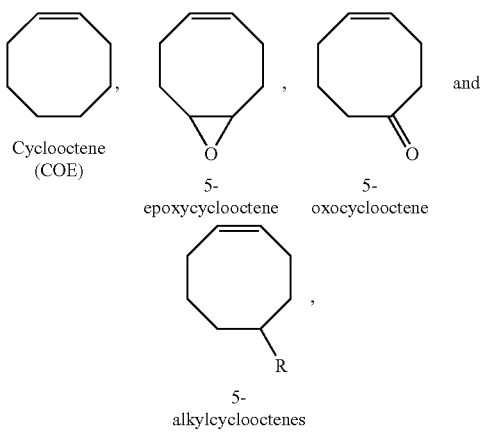

in which R is an alkyl group comprising from 1 to 22, preferably from 1 to 14, carbon atoms, are preferred according to the invention; cyclooctene being most particularly preferred. For example, R is an n-hexyl group.

The cyclic compounds of formula (B) are preferably, according to the invention, chosen from the group formed by norbornene (NBN), dicyclopentadiene and 7-oxanorbornene, which have the following respective formulae:

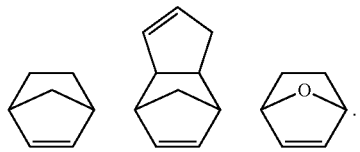

The cyclic compounds of formula (B) may also be chosen from the group formed by the compounds having the following formulae:

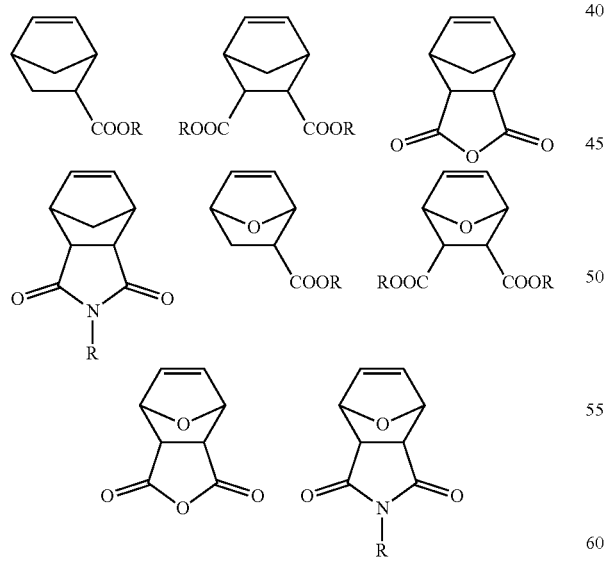

in which: R is an alkyl group comprising from 1 to 22, preferably from 1 to 14, carbon atoms. For example, R is an n-hexyl group.

The cyclic compounds of formula (B) may also be chosen from the group formed by the addition products (or adducts) resulting from the Diels-Alder reaction using cyclopentadiene or furan as starting material, and also the compounds derived from norbornene as described in WO 2001/04173 (such as: norbornene isobornyl carboxylate, norbornene phenyl carboxylate, norbornene ethylhexyl carboxylate, norbornene phenoxyethyl carboxylate and alkyl norbornene dicarboximide, the alkyl usually comprising from 3 to 8 carbon atoms), and those described in WO 2011/038057 (norbornene dicarboxylic anhydrides and optionally 7-oxanorbornene dicarboxylic anhydrides).

According to a first embodiment of the preparation process according to the invention (referred to as the "monofunctional CTA route"), the CTA used is of formula (C1) defined previously and may also be represented as follows, with p1, X, A, R9, R10 and R11 having the meanings given previously:

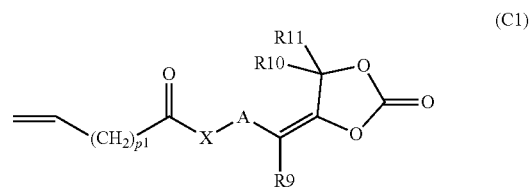

In this case, preferably:
p1=0,
X is an oxygen atom or a group NR12 in which R12 is a methyl group,
A is a C1-C6 alkylene group,
R9 is a hydrogen atom,
R10 and R11 are methyl groups.

The compound of formula (C1) may be obtained according to scheme (1) below, by following the procedures described in patent applications DE1098953 and DE3433403, p1, X, A, R9, R10 and R11 having the meanings given previously:

Scheme (1)

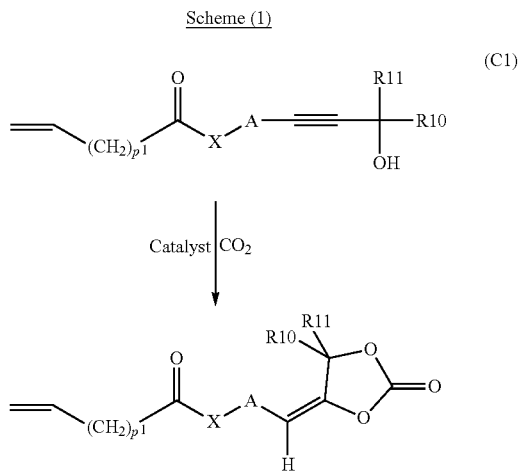

According to a second embodiment of the preparation process according to the invention (referred to as the "difunctional CTA route"), the CTA2 is of formula (C2) defined previously and may also be represented as follows, with p1, p2, Z, X, A, R9, R10, R11 and ⌇ having the meanings given previously:

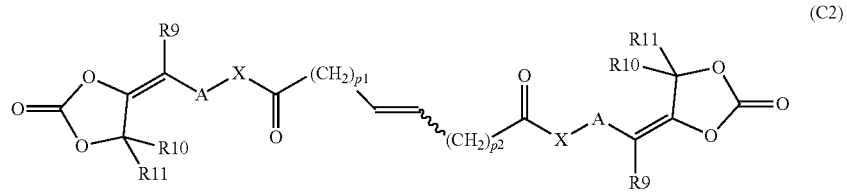

(C2)

In this case, preferably:
p1 or p2=0, and more preferentially p1=p2=0,
X is an oxygen atom or a group NR12 in which R12 is a methyl group,
A is a C1-C6 alkylene group,
R9 is a hydrogen atom,
R10 and R11 are methyl groups.

The compound of formula (C2) may be obtained according to scheme (2) below, corresponding to a novel variant of scheme (1), p1, p2, X, A, R9, R10 and R11 having the meanings given previously:

Scheme (2)

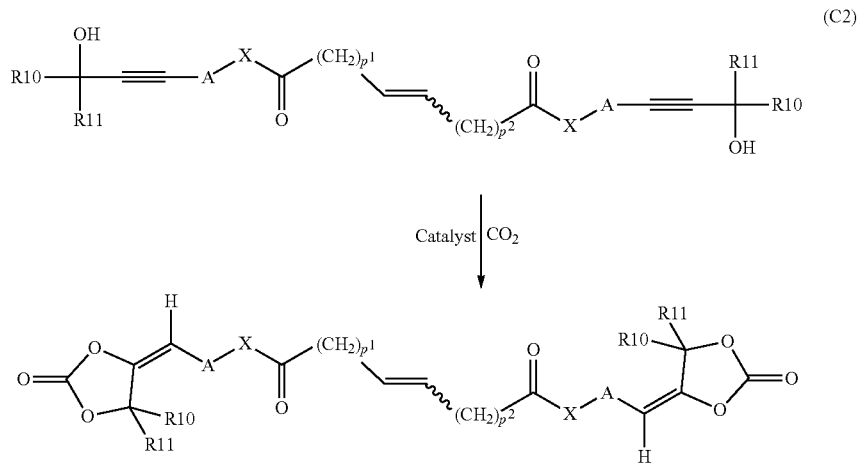

The step of ring-opening metathesis polymerization is usually performed in the presence of at least one solvent, generally chosen from the group formed by the aqueous or organic solvents typically used in polymerization reactions and which are inert under the polymerization conditions described above.

As examples of solvents that may be used, mention may be made, for example, of aromatic hydrocarbons, chlorinated hydrocarbons, ethers, aliphatic hydrocarbons, alcohols and water, or mixtures thereof.

The solvent is preferably chosen from the group formed by benzene, toluene, para-xylene, methylene chloride, dichloroethane, dichlorobenzene, chlorobenzene, tetrahydrofuran, diethyl ether, pentane, hexane, heptane, methanol, ethanol and water, or mixtures thereof.

More preferentially, the solvent is chosen from the group formed by benzene, toluene, para-xylene, methylene chloride, dichloroethane, dichlorobenzene, chlorobenzene, tetrahydrofuran, diethyl ether, pentane, hexane, heptane, methanol, ethanol, and mixtures thereof.

Better still, the solvent is toluene, heptane or a mixture of toluene and methylene chloride. The solubility of the polymer formed during the polymerization reaction depends generally and mainly on the choice of the solvent and on the molar mass of the polymer obtained. It is also possible for the reaction to be performed without solvent.

The metathesis catalyst, for instance a Grubbs catalyst, is generally a commercial product.

The metathesis catalyst is usually a catalyst comprising at least one transition metal, such as ruthenium, usually in complex form.

Preferably, the metathesis catalyst is chosen from ruthenium complexes such as a ruthenium-carbene complex.

More preferentially, the metathesis catalyst is chosen from Grubbs catalysts.

The term "Grubbs catalyst" generally means, according to the invention, a $1^{st}$ or $2^{nd}$ generation Grubbs catalyst, but also any other catalyst of Grubbs type (of ruthenium-carbene type) accessible to a person skilled in the art, for instance the substituted Grubbs catalysts described in patent U.S. Pat. No. 5,849,851.

A $1^{st}$ generation Grubbs catalyst is generally of formula (G1):

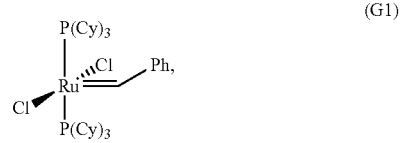

in which:
Ph is a phenyl group,
Cy is a cyclohexyl group, and
$P(Cy)_3$ is a tricyclohexylphosphine group.

The IUPAC name of the catalyst (G1) is: benzylidenebis(tricyclohexylphosphine)dichlororuthenium (of CAS number 172222-30-9).

A $2^{nd}$ generation Grubbs catalyst is generally of formula (G2):

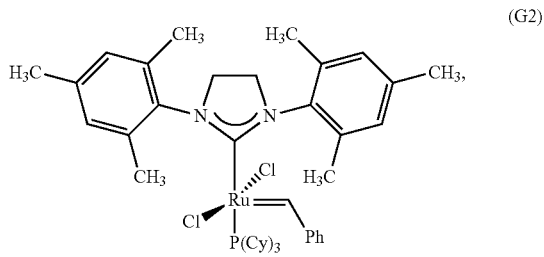

in which:
Ph is a phenyl group,
Cy is a cyclohexyl group, and
P(Cy)$_3$ is a tricyclohexylphosphine group.

The IUPAC name of the catalyst (G2) is: benzylidene[1,3-bis(2,4,6-trimethylphenyl)-2-imidazolidinylidene]dichloro(tricyclohexylphosphine)ruthenium (of CAS number 246047-72-3).

Preferably, the catalyst is a $2^{nd}$ generation Grubbs catalyst, as defined, for example, by formula (G2).

The invention also relates to a process for preparing a polyurethane, comprising the reaction of at least one hydrocarbon-based polymer bearing exo-vinylene cyclocarbonate end groups according to the invention, which may especially be obtained via the preparation process according to the invention, with at least one compound comprising at least one, preferably at least two, amine groups, chosen, for example, from monoamines, diamines, triamines and other polyamines; and also to the polyurethanes that may be obtained via this preparation process.

The amine compounds described above are preferably such that at least one amine group, preferably all the amine groups, are primary amine groups. These amine compounds may be oligomers. These oligomers generally have a number-average molar mass of less than 2000.

Preferably, the hydrocarbon-based polymer(s) bearing exo-vinylene cyclocarbonate end groups and amine compound(s) are used in amounts such that all of the exo-vinylene cyclocarbonate groups of the polymer(s) have reacted with an amine group of an amine compound to form a urethane group.

More preferentially, the hydrocarbon-based polymer(s) bearing exo-vinylene cyclocarbonate end groups are reacted with one or more primary (poly)amines in stoichiometric amounts, i.e. the mole ratio of the number of cyclocarbonate groups to the number of primary amine groups is approximately equal to 1.

The polyurethanes thus obtained, which are novel, were advantageously prepared without isocyanate.

These polyurethanes, once formulated (i.e. placed in formulation with other optional additives), are intended to be used as such as coating, mastic or adhesive compositions, or in coating, mastic or adhesive compositions, for example as fillers and/or as resins. It is also possible to formulate independently the polymer bearing exo-vinylene cyclocarbonate end groups according to the invention and the compound comprising at least one amine group, before mixing them, especially in the form of a two-pack composition.

The invention will be understood more clearly in the light of the examples that follow.

EXAMPLES

The examples that follow illustrate the invention without, however, limiting its scope.

I) Examples 1 to 9: Synthesis of a Polymer Bearing Exo-Vinylene Cyclocarbonate End Groups According to the Invention The hydrocarbon-based polymers bearing exo-vinylene cyclocarbonate end groups of Examples 1 to 9 were obtained by means of the following steps:
1—a step of synthesis of the cycloolefin(s) of formulae (A) and/or (B),
2—a step of synthesis of the transfer agent (CTA) of formula (C1) or (C2),
3—a step of ring-opening metathesis polymerization of a cycloolefin of formula (A) and optionally of a compound of formula (B) in the presence of a Grubbs catalyst and of the transfer agent, step 1 preferably being optional when the cycloolefin(s) of formulae (A) and (B) are commercially available.

The ring-opening metathesis polymerization reactions performed in Examples 1 to 9 are represented by the general schemes (3) and (4), using, respectively, a monofunctional CTA (C1) and a difunctional CTA (C2), and will be explained in each individual case in the examples.

Scheme (3)

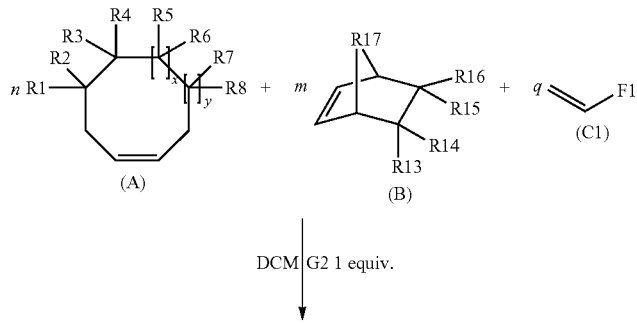

DCM | G2 1 equiv.

-continued

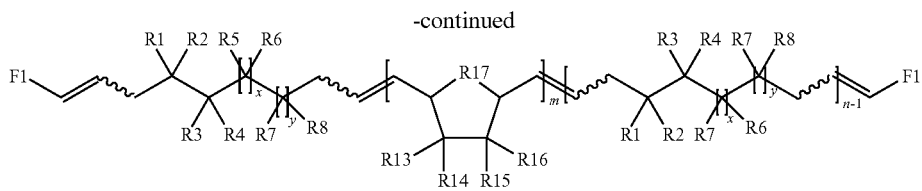

Scheme (4)

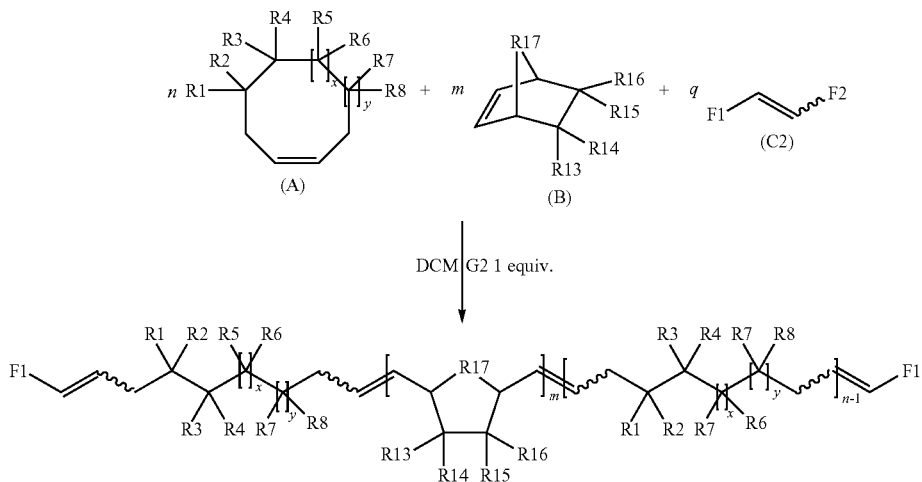

In these schemes (3) and (4):
1 equiv. means one equivalent and corresponds to the amount of metathesis catalyst used;
DCM means dichloromethane;
(A) and (B) are the cycloolefins corresponding, respectively, to formulae (A) and (B) defined previously;
(C1) and (C2) are the transfer agents corresponding, respectively, to formulae (C1) and (C2) defined previously;
the ⌇ bond is a carbon-carbon single bond geometrically oriented on one side or the other relative to the double bond (cis or trans) for (C2);
G2 is the metathesis catalyst of formula (G2) as defined previously;
F1 and F2 are identical and both correspond:
either to the group of ester type below:

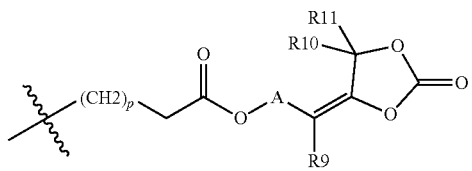

or to the group of amide type:

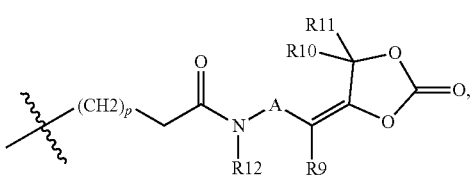

in which: p=p1 or p2, and A, R9, R10 and R11 are as defined previously;

n is the number of moles of cycloolefin(s) of formula (A);
m is the number of moles of cycloolefin(s) of formula (B);
q is the number of moles of CTA of formula (C1) or (C2).

The number of monomer units in the polymer obtained on conclusion of the polymerization reaction is equal to n+m.

In each of the Examples 1 to 9 described below, the reaction lasts 24 hours (h) at a temperature of 40° C.

All the polymerizations were performed in a similar manner. The only differences lie in the nature and the initial concentration of the chain-transfer agent(s) (CTA) of type (C1) or (C2) used.

The CTAs used in Examples 1 to 9 are the following:

[(5,5-dimethyl-2-oxo-1,3-dioxolan-4-ylidene)propyl] acrylate (noted CTA$^1$)

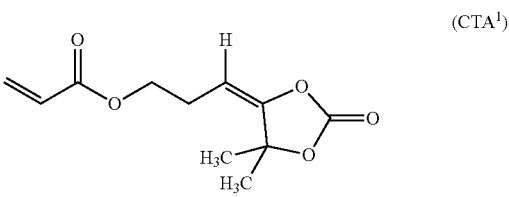 [SMILES: C=CC(=O)OCC/C=C1/OC(=O)OC1(C)C]

(which corresponds to a CTA of formula (C1) in which: p1=0, X is an oxygen atom, A is an ethylene group —CH2-CH2-, R9 is a hydrogen atom, R10 and R11 are methyl groups);

[N-methyl(5,5-dimethyl-2-oxo-1,3-dioxolan-4-ylidene)propyl]acrylamide (noted CTA²)

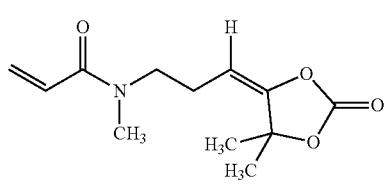

(CTA²)

(which corresponds to a CTA of formula (C1) in which: p1=0, X is an N—CH3 group with R12 being a methyl group, A is an ethylene group —CH2-CH2-, R9 is a hydrogen atom, R10 is a methyl group, R11 and R12 are methyl groups);

bis[(5,5-dimethyl-2-oxo-1,3-dioxolan-4-ylidene)propyl] fumarate (noted CTA³)

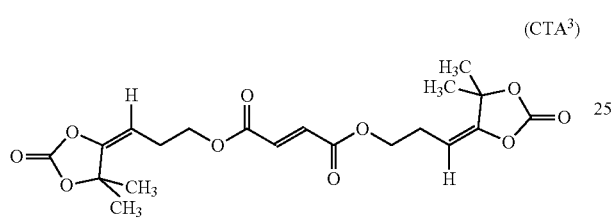

(CTA³)

(which corresponds to a CTA of formula (C2) in which: p1=p2=0, X is an oxygen atom, A is an ethylene group —CH2-CH2-, R9 is a hydrogen atom, R10 and R11 are methyl groups); and bis[(5,5-dimethyl-2-oxo-1,3-dioxolan-4-ylidene)propyl]fumaramide (noted CTA⁴)

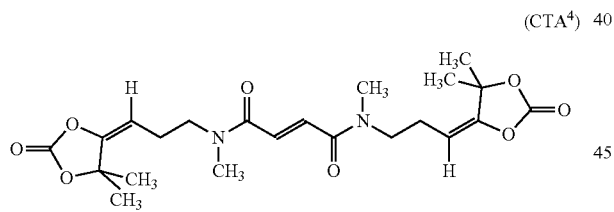

(CTA⁴)

(which corresponds to a CTA of formula (C2) in which: p1=p2=0, X is an N—CH3 group with R12 being a methyl group, A is an ethylene group —CH2-CH2-, R9 is a hydrogen atom, R10 and R11 are methyl groups).

Two reaction possibilities (i and ii) exist, depending on whether the cycloolefin of formula (A) is used alone (Examples 1 to 7) or depending on whether the cycloolefins of formulae (A) and (B) are used as a mixture (Examples 8 and 9).

i—Examples 1 to 7: Polymerization of the Cycloolefins of Formula (A)

The cycloolefins of formula (A) used in Examples 1 to 7 are as follows:

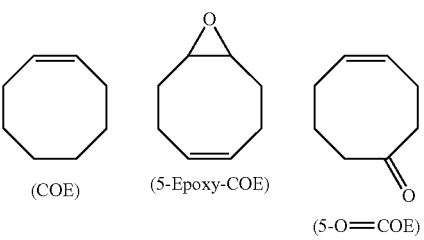

(COE)    (5-Epoxy-COE)    (5-O═COE)

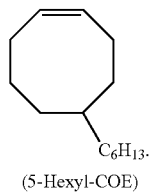

(5-Hexyl-COE)

Cyclooctene (COE) and 5,6-epoxycyclooctene (5-epoxy-COE) are commercial products from the company Sigma-Aldrich.

5-Oxocyclooctene (5-O═COE) and 5-n-hexylcyclooctene (5-hexyl-COE) may be synthesized from 5,6-epoxycyclooctene (5-epoxy-COE) according to the route indicated in reaction scheme (5) below:

Scheme (5)

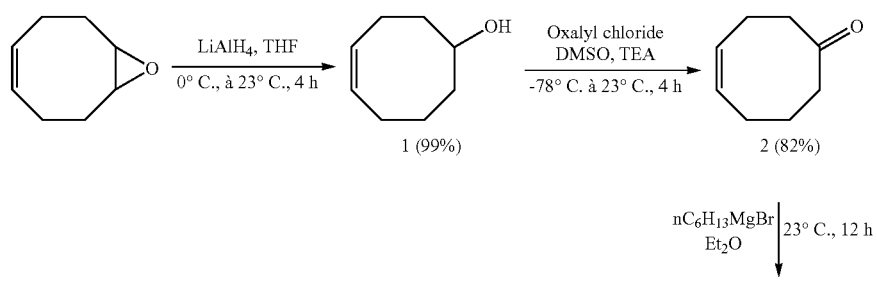

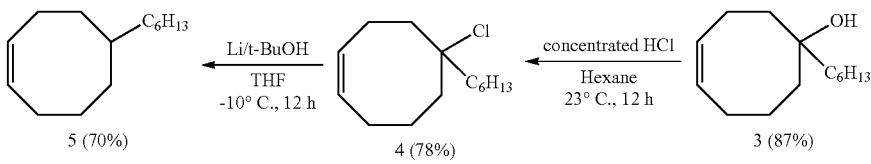

5-Oxocyclooctene (5-O=COE, referenced 2 in scheme (5) above) was synthesized according to the procedure indicated in the publication by A. Diallo et al., Polymer Chemistry, Vol. 5, Issue 7, 7 Apr. 2014, pages 2583-2591 (which referred to Hillmyer et al., Macromolecules, 1995, 28, pages 6311-6316).

5-Hexylcyclooctene (5-hexyl-COE referenced 5 in scheme (5) above) was synthesized according to the procedure indicated in the abovementioned publication by A. Diallo et al., Polymer Chemistry (which referred to Kobayashi et al., J. Am. Chem. Soc., 2011, 133, pages 5794-5797).

The starting materials, reagents and solvents used for the synthesis of these cycloolefins of formula (A) are commercially available from the company Sigma-Aldrich.

In the examples that follow:
the NMR spectra were recorded on Brüker AM-500 and Brüker AM-400 spectrometers, at 298 K in CDCl$_3$. The chemical shifts were referenced with respect to tetramethylsilane (TMS) using the ($^1$H) or ($^{13}$C) resonance of the deuterated solvents.
the number-average and weight-average molar masses ($M_n$ and $M_w$) and the polydispersity PDI ($M_w/M_n$) of the polymers were determined by size exclusion chromatography (SEC), with PS calibration using a Polymer Laboratories PL-GPC 50 machine.

Example 1: Synthesis of a Polymer Comprising Two [(5,5-dimethyl-2-oxo-1,3-dioxolan-4-ylidene) propyl] ester End Groups Starting with cyclooctene (COE) and [(5,5-dimethyl-2-oxo-1,3-dioxolan-4-ylidene)propyl] acrylate (CTA$^1$)

The reaction was performed according to scheme (6) below, in a mole ratio m/n equal to 0/100 and according to the procedure described below:

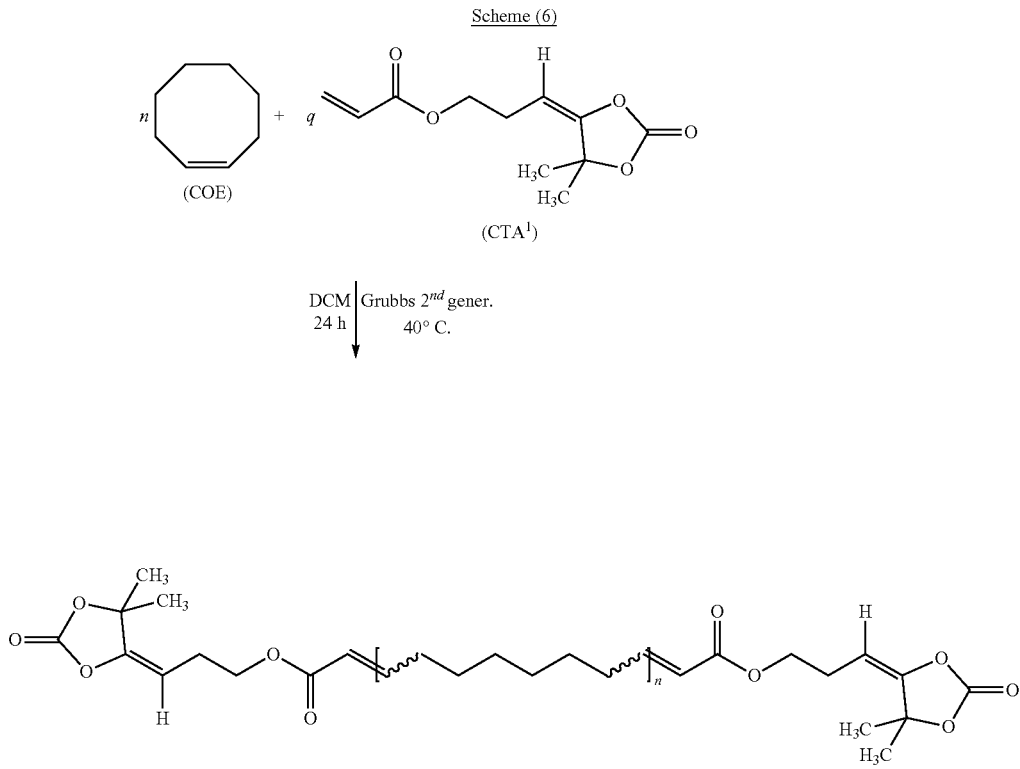

Procedure:

The cycloolefin of formula (A) (108.00 mmol), hydroquinone (0.54 mmol) and dry $CH_2Cl_2$ (50 mL) were mixed in a 1000 mL round-bottomed flask. The round-bottomed flask and its contents were then placed under argon. The CTA (10.80 mmol) of type (C1) was introduced into the round-bottomed flask using a syringe. The round-bottomed flask was then immersed in an oil bath at 40° C. and the catalyst G2 (54.00 μmol) in solution in $CH_2Cl_2$ (20 mL) was then immediately added using a cannula. 24 hours after the addition of the catalyst, the product is extracted from the round-bottomed flask after evaporating off the solvent under vacuum. The product is then recovered after precipitating from methanol, filtering and drying at 20° C. under vacuum.

Results:

The polymer obtained is solid at room temperature.

The degree of conversion of the cycloolefin of formula (A) determined by NMR (expressed in %), the number-average molar mass of the polymer obtained (expressed in grams per mol) and the polydispersity (PDI) of said polymer, determined by SEC, gave the following results:

TABLE 1

| Test no. | [A]/[CTA$^1$]/[Ru] (mol/mol) | Conversion A (%) | Mn$_{SEC}$ (g/mol) | PDI |
|---|---|---|---|---|
| 1 | 2 000/200/1 | 100 | 4 600 | 1.53 |

The $^1$H (CDCl$_3$, 500 MHz, 298 K) and $^{13}$C (CDCl$_3$, 100 MHz, 298 K) NMR analyses for the polymer obtained for this test confirmed the structure of the expected polymer as represented in scheme (6).

Example 2: Synthesis of a Polymer Comprising Two [N-methyl(5,5-dimethyl-2-oxo-1,3-dioxolan-4-ylidene)propyl]amide End Groups Starting with cyclooctene (COE) and [N-methyl(5,5-dimethyl-2-oxo-1,3-dioxolan-4-ylidene)propyl]acrylamide (CTA$^2$)

The reaction was performed according to scheme (7) below, in a mole ratio m/n equal to 0/100 and according to the procedure of Example 1:

Results:

The polymer obtained is solid at room temperature.

The degree of conversion of the cycloolefin of formula (A) determined by NMR (expressed in %), the number-average molar mass of the polymer obtained (expressed in grams per mol) and the polydispersity (PDI) of said polymer, determined by SEC, gave the following results:

TABLE 2

| Test no. | [A]/[CTA$^2$]/[Ru] (mol/mol) | Conversion A (%) | Mn$_{SEC}$ (g/mol) | PDI |
|---|---|---|---|---|
| 2 | 2 000/200/1 | 100 | 4 900 | 1.49 |

The $^1$H (CDCl$_3$, 500 MHz, 298 K) and $^{13}$C (CDCl$_3$, 100 MHz, 298 K) NMR analyses for the polymer obtained for this test confirmed the structure of the expected polymer as represented in scheme (7).

Example 3: Synthesis of a Polymer Comprising Two [(5,5-dimethyl-2-oxo-1,3-dioxolan-4-ylidene)propyl] ester End Groups Starting with cyclooctene (COE) and bis[(5,5-dimethyl-2-oxo-1,3-dioxolan-4-ylidene)propyl] fumarate (CTA$^3$)

The reaction was performed according to scheme (8) below, in a mole ratio m/n equal to 0/100 and according to the procedure described below:

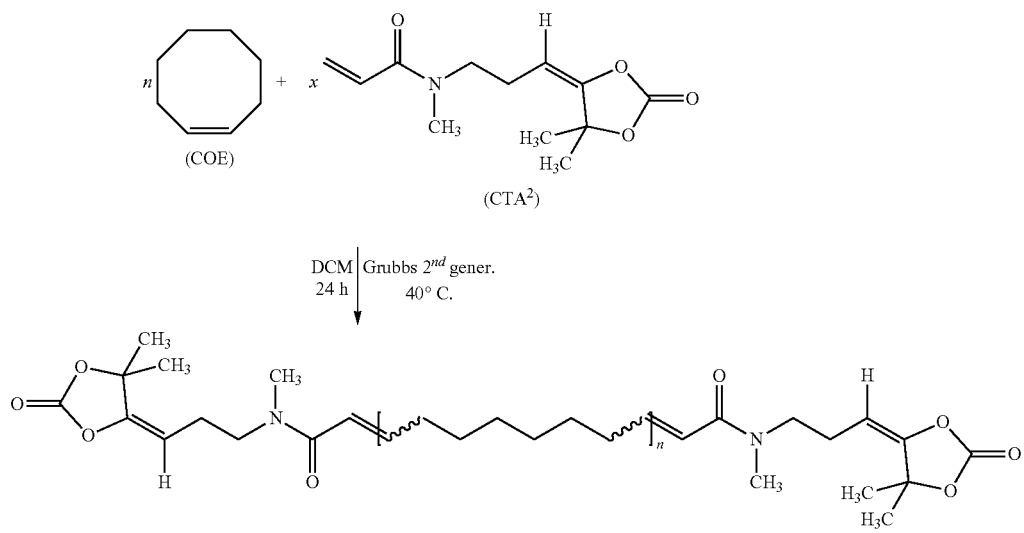

Scheme (8)

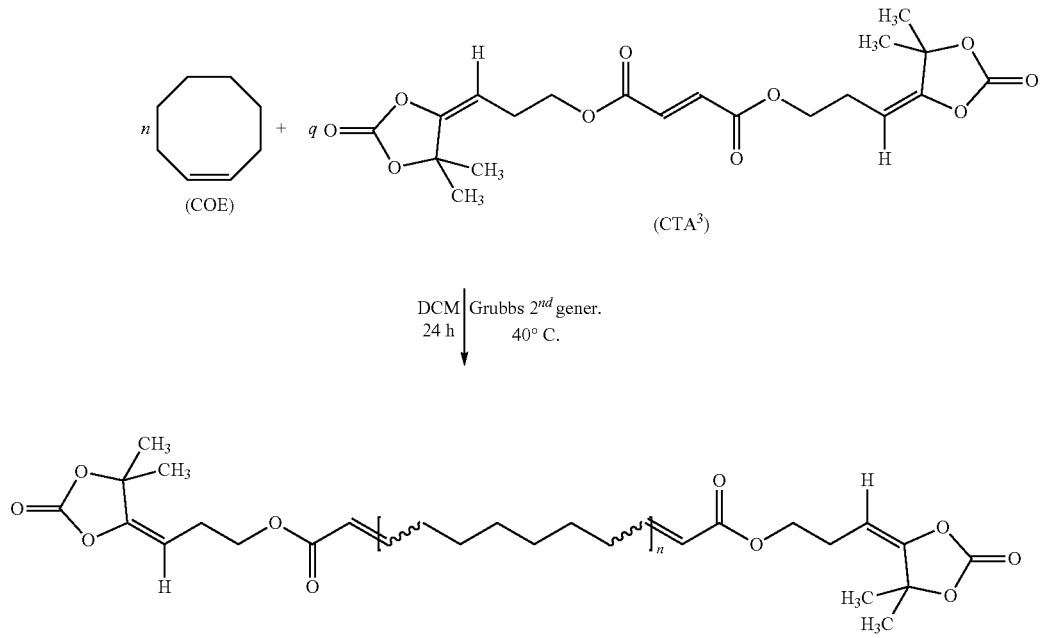

Procedure:

The cycloolefin of formula (A) (108.00 mmol), hydroquinone (0.54 mmol) and dry $CH_2Cl_2$ (50 mL) were mixed in a 1000 mL round-bottomed flask. The round-bottomed flask and its contents were subsequently placed under argon. The CTA (5.40 mmol) of type (C2) was introduced into the round-bottomed flask using a syringe. The round-bottomed flask was then immersed in an oil bath at 40° C., and the catalyst G2 (54.00 µmol) in solution in $CH_2Cl_2$ (20 mL) was then immediately added using a cannula. 24 hours after the addition of the catalyst, the product is extracted from the round-bottomed flask after evaporating off the solvent under vacuum. The product is then recovered after precipitating from methanol, filtering and drying at 20° C. under vacuum.

Results:

The polymer obtained is solid at room temperature.

The results for the degree of conversion of the cycloolefin of formula (A) determined by NMR (expressed in %), the number-average molar mass of the polymer obtained (expressed in grams per mol) and the polydispersity (PDI) of said polymer, determined by SEC, are given in table 3 below.

The $^1H$ ($CDCl_3$, 500 MHz, 298 K) and $^{13}C$ ($CDCl_3$, 100 MHz, 298 K) NMR analyses for the polymer obtained for this test confirmed the structure of the expected polymer as represented in scheme (8).

Example 4: Synthesis of a Polymer Comprising Two [(5,5-dimethyl-2-oxo-1,3-dioxolan-4-ylidene)propyl]amide End Groups Starting with cyclooctene (COE) and bis[(5,5-dimethyl-2-oxo-1,3-dioxolan-4-ylidene)propyl]fumaramide ($CTA^4$)

The reaction was performed according to scheme (9) below, in a mole ratio m/n equal to 0/100 and according to the procedure of Example 3:

Scheme (9)

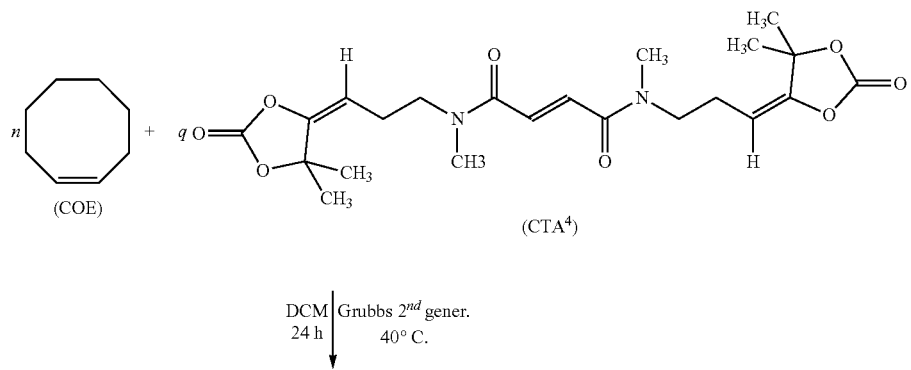

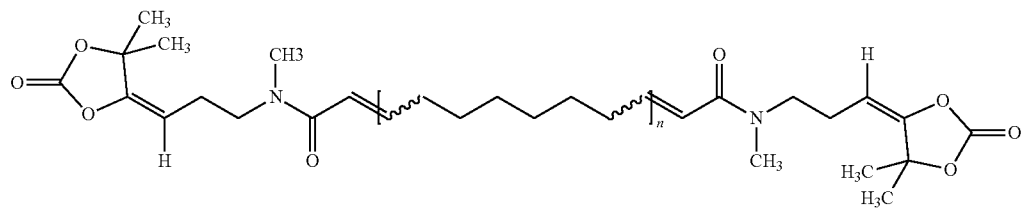

Results:

The polymer obtained is solid at room temperature.

The results for the degree of conversion of the cycloolefin of formula (A) determined by NMR (expressed in %), the number-average molar mass of the polymer obtained (expressed in grams per mol) and the polydispersity (PDI) of said polymer, determined by SEC, are given in table 3 below.

The $^1$H (CDCl$_3$, 500 MHz, 298 K) and $^{13}$C (CDCl$_3$, 100 MHz, 298 K) NMR analyses for the polymer obtained for this test confirmed the structure of the expected polymer as represented in scheme (9).

Example 5: Synthesis of a Polymer Comprising Two [(5,5-dimethyl-2-oxo-1,3-dioxolan-4-ylidene) propyl] ester End Groups Starting with cyclooctene monoepoxide (5-Epoxy-COE) and bis[(5,5-dimethyl-2-oxo-1,3-dioxolan-4-ylidene)propyl] fumarate (CTA$^3$)

The reaction was performed according to scheme (10) below, in a mole ratio m/n equal to 0/100 and according to the procedure of Example 3:

Results:

The polymer obtained is liquid at room temperature.

The results for the degree of conversion of the cycloolefin of formula (A) determined by NMR (expressed in %), the number-average molar mass of the polymer obtained (expressed in grams per mol) and the polydispersity (PDI) of said polymer, determined by SEC, are given in table 3 below.

The $^1$H (CDCl$_3$, 500 MHz, 298 K) and $^{13}$C (CDCl$_3$, 100 MHz, 298 K) NMR analyses for the polymer obtained for this test confirmed the structure of the expected polymer as represented in scheme (10).

Example 6: Synthesis of a Polymer Comprising Two [(5,5-dimethyl-2-oxo-1,3-dioxolan-4-ylidene) propyl] ester End Groups Starting with 5-oxocyclooctene (5-O=COE) and bis[(5,5-dimethyl-2-oxo-1,3-dioxolan-4-ylidene)propyl] fumarate (CTA$^3$)

The reaction was performed according to scheme (11) below, in a mole ratio m/n equal to 0/100 and according to the procedure of Example 3:

Scheme (10)

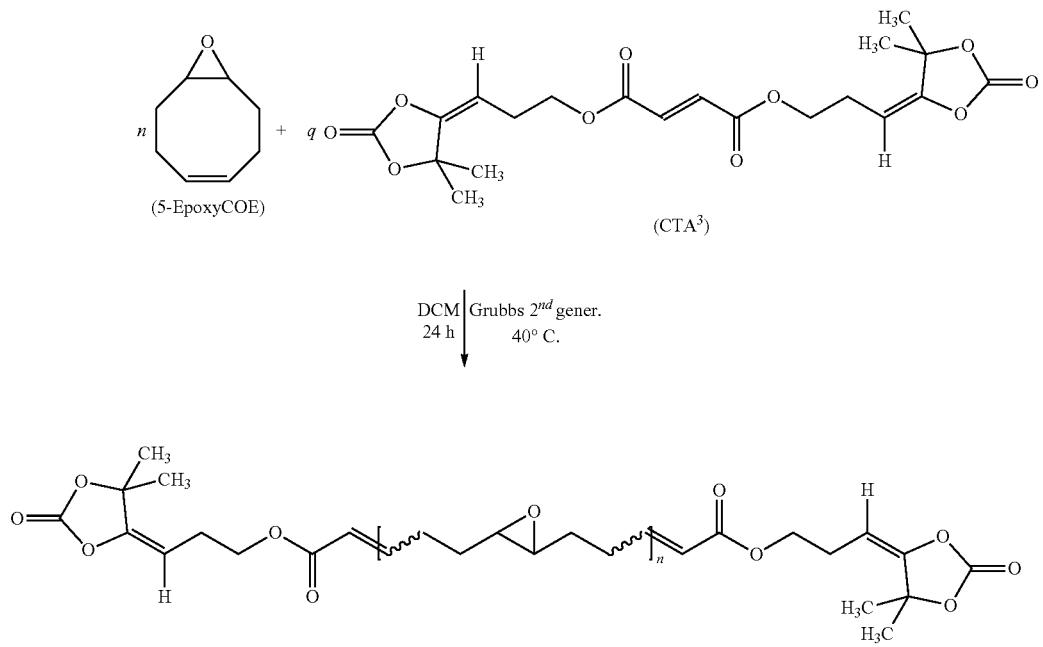

Scheme (11)

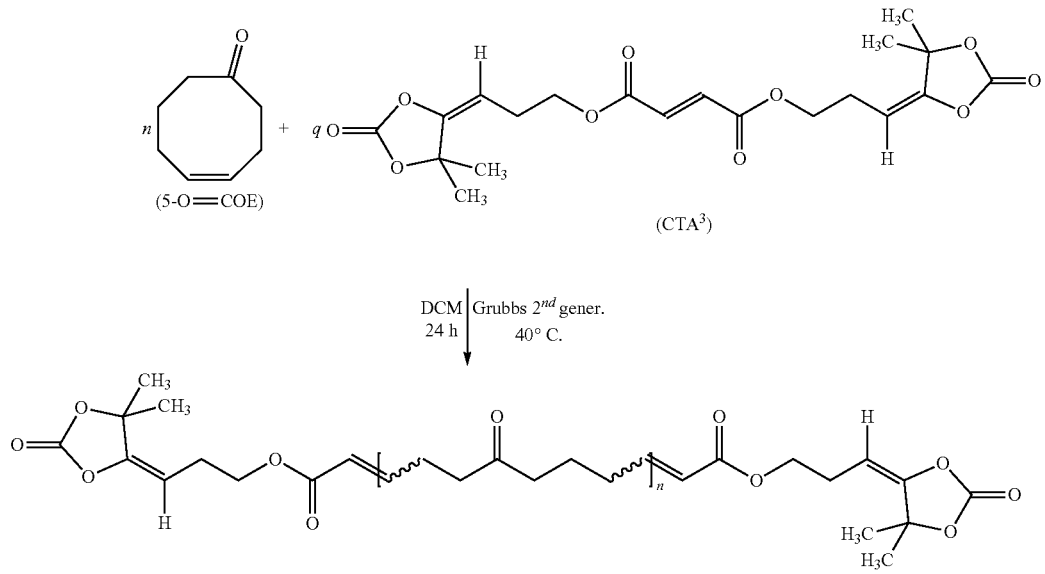

Results:

The polymer obtained is solid at room temperature.

The results for the degree of conversion of the cycloolefin of formula (A) determined by NMR (expressed in %), the number-average molar mass of the polymer obtained (expressed in grams per mol) and the polydispersity (PDI) of said polymer, determined by SEC, are given in table 3 below.

The $^1$H (CDCl$_3$, 500 MHz, 298 K) and $^{13}$C (CDCl$_3$, 100 MHz, 298 K) NMR analyses for the polymer obtained for this test confirmed the structure of the expected polymer as represented in scheme (11).

Example 7: Synthesis of a Polymer Comprising Two [(5,5-dimethyl-2-oxo-1,3-dioxolan-4-ylidene)propyl] ester End Groups Starting with 5-hexylcyclooctene (5-Hexyl-COE) and bis[(5,5-dimethyl-2-oxo-1,3-dioxolan-4-ylidene)propyl] fumarate (CTA$^3$)

The reaction was performed according to scheme (12) below, in a mole ratio m/n equal to 0/100 and according to the procedure of Example 3:

Scheme (12)

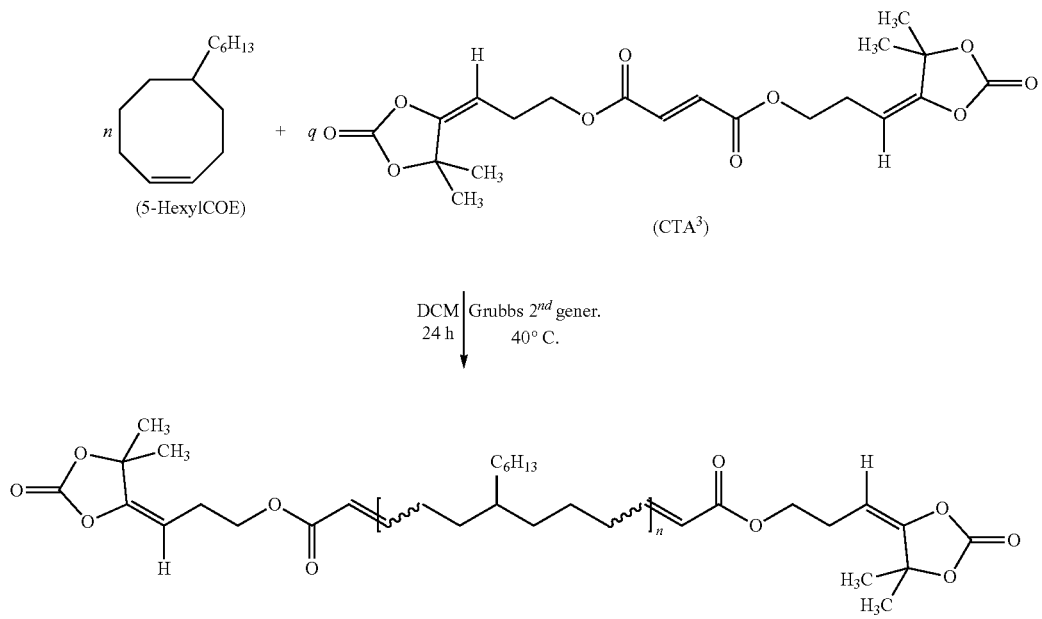

Results:

The polymer obtained is liquid at room temperature.

The results for the degree of conversion of the cycloolefin of formula (A) determined by NMR (expressed in %), the number-average molar mass of the polymer obtained (expressed in grams per mol) and the polydispersity (PDI) of said polymer, determined by SEC, are given in table 3 below.

Example 8: Synthesis of a Polymer Comprising Two Exo-Vinylene Cyclocarbonate End Groups Starting with Cyclooctene (COE), Norbornene (NBN) and bis[(5,5-dimethyl-2-oxo-1,3-dioxolan-4-ylidene)propyl] fumarate ($CTA^3$)

The reaction was performed according to scheme (13) below, in a mole ratio m/n equal to 50/50 and according to the procedure described below:

Scheme (13)

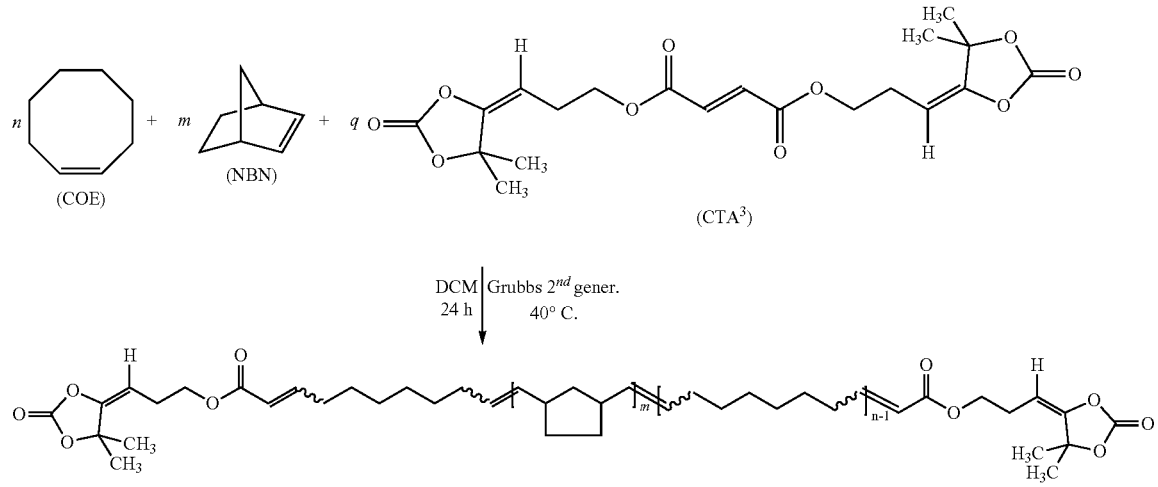

TABLE 3

| Test no. | [A]/[$CTA^3$]/[Ru] (mol/mol) | Conversion A (%) | $Mn_{SEC}$ (g/mol) | PDI |
|---|---|---|---|---|
| 3 | 2 000/100/1 | 100 | 5 100 | 1.53 |
| 4 | 2 000/100/1 | 100 | 5 200 | 1.47 |
| 5 | 2 000/100/1 | 100 | 4 800 | 1.50 |
| 6 | 2 000/100/1 | 100 | 5 000 | 1.51 |
| 7 | 2 000/100/1 | 100 | 5 300 | 1.52 |

The $^1H$ (CDCl$_3$, 500 MHz, 298 K) and $^{13}C$ (CDCl$_3$, 100 MHz, 298 K) NMR analyses for the polymer obtained for this test confirmed the structure of the expected polymer as represented in scheme (12).

ii) Examples 8 to 9—Polymerization of a Mixture of Cycloolefins of Formulae (A) and (B)

The cycloolefins of formulae (A) and (B) used in Examples 8 and 9 are, respectively, as follows:

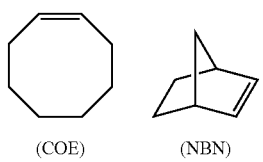

(COE) (NBN)

Cyclooctene (COE) with a purity of greater than 95% and norbornene (NBN) with a purity of greater than 99% are commercially available from the company Sigma-Aldrich. These products were distilled beforehand over CaH$_2$, before being used in Examples 8 and 9.

Procedure:

The cycloolefins of formulae (A) and (B), corresponding to COE (54.00 mmol) and NBN (54.00 mmol), respectively, hydroquinone (0.54 mmol) and dry CH$_2$Cl$_2$ (50 mL) were mixed in a 1000 mL round-bottomed flask. The round-bottomed flask and its contents were subsequently placed under argon. The CTA (5.40 mmol) of type (C2) was then introduced into the round-bottomed flask using a syringe. The round-bottomed flask was then immersed in an oil bath at 40° C. and the catalyst G2 (54 μmol) in solution in CH$_2$Cl$_2$ (20 mL) was then immediately added using a cannula. 24 hours after the addition of the catalyst, the product was extracted from the round-bottomed flask after evaporating off the solvent under vacuum. The product was then recovered after precipitating from methanol, filtering and drying at 20° C. under vacuum.

Results:

The polymer obtained is liquid at room temperature.

The degrees of conversion of the cycloolefins of formulae (A) and (B) determined by NMR (expressed in %), the number-average molar mass of the polymer obtained (expressed in grams per mol) and the polydispersity (PDI) of the polymer, determined by SEC. The results are given in table 4 below.

TABLE 4

| Test no. | [A]/[B]/[$CTA^1$]/[Ru] (mol/mol) | Conversion (%) | $Mn_{SEC}$ (g/mol) | PDI |
|---|---|---|---|---|
| 8 | 1 000/1 000/100/1 | 100 | 5 000 | 1.60 |

The $^1H$ (CDCl$_3$, 500 MHz, 298 K) and $^{13}C$ (CDCl$_3$, 100 MHz, 298 K) NMR analyses for the polymer obtained confirmed the structure of the expected polymer as represented in scheme (13).

Example 9: Synthesis of a Polymer Comprising Two Exo-Vinylene Cyclocarbonate End Groups Starting with Cyclooctene (COE), Norbornene (NBN) and bis[(5,5-dimethyl-2-oxo-1,3-dioxolan-4-ylidene)propyl]fumaramide (CTA⁴)

The reaction was performed according to scheme (14) below, in a mole ratio m/n equal to 50/50 and according to the same procedure as Example 8:

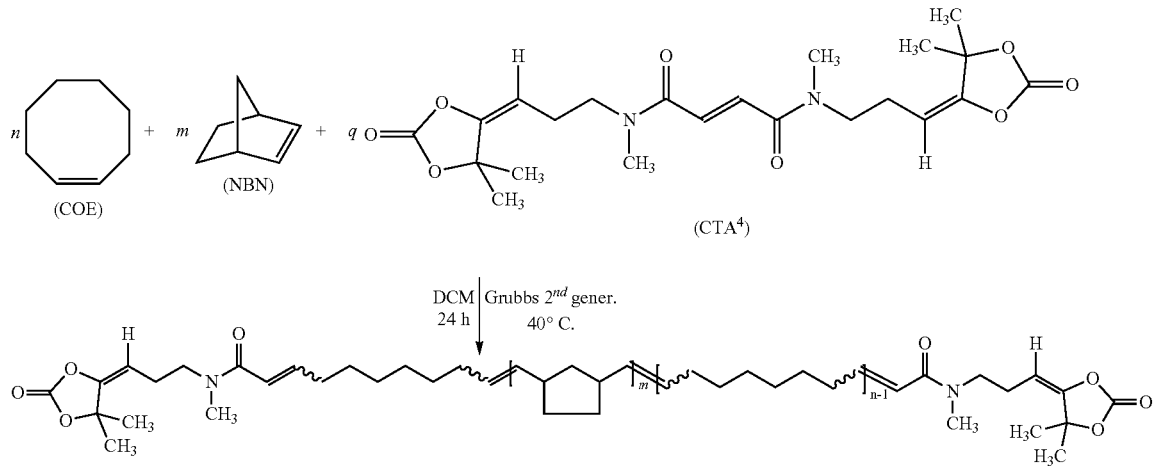

Scheme (14)

Results:

The polymer obtained is liquid at room temperature.

The degrees of conversion of the cycloolefins of formulae (A) and (B) determined by NMR (expressed in %), the number-average molar mass of the polymer obtained (expressed in grams per mol) and the polydispersity (PDI) of the polymer, determined by SEC. The results are given in table 5 below.

TABLE 5

| Test no. | [A]/[B]/[CTA³]/[Ru] (mol/mol) | Conversion (%) | $Mn_{SEC}$ (g/mol) | PDI |
|---|---|---|---|---|
| 9 | 1 000/1 000/100/1 | 100 | 5 300 | 1.58 |

The $^1$H (CDCl₃, 500 MHz, 298 K) and $^{13}$C (CDCl₃, 100 MHz, 298 K) NMR analyses for the polymer obtained confirmed the structure of the expected polymer as represented in scheme (14).

II—Comparative Example 10: Synthesis of a Polymer Comprising Two methylene cyclocarbonate End Groups Starting with cyclooctene (COE) and bis[(2-oxo-1,3-dioxolan-4-yl)methyl] fumarate (CTA⁵)

The reaction was performed according to scheme (15) below, in a mole ratio m/n equal to 0/100 and according to the same procedure as Example 3:

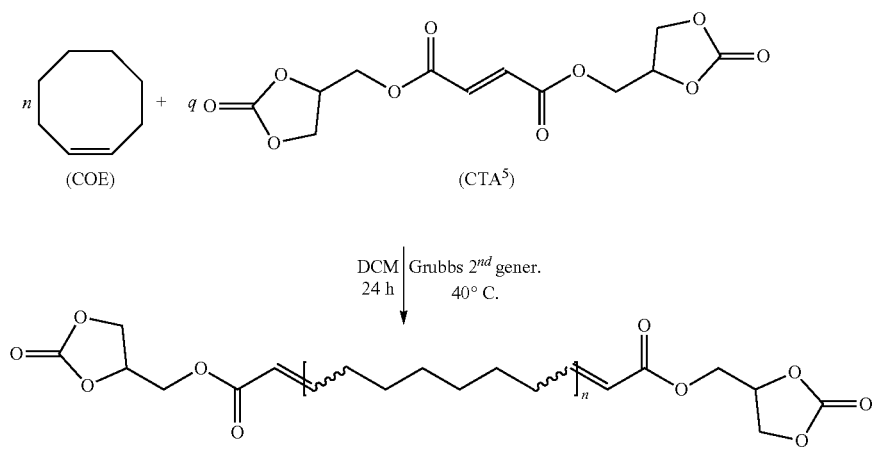

Scheme (15)

Results:

The polymer obtained is solid at room temperature.

The results for the degree of conversion of the cycloolefin of formula (A) determined by NMR (expressed in %), the number-average molar mass of the polymer obtained (expressed in grams per mol) and the polydispersity (PDI) of said polymer, determined by SEC, are given in table 6 below:

TABLE 6

| Test no. | [A]/[B]/[CTA¹]/[Ru] (mol/mol) | Conversion (%) | $Mn_{SEC}$ (g/mol) | PDI |
|---|---|---|---|---|
| 8 | 1 000/1 000/100/1 | 100 | 5 000 | 1.60 |

The ¹H (CDCl₃, 500 MHz, 298 K) and ¹³C (CDCl₃, 125 MHz, 298 K) NMR analyses for the polymer obtained for this test confirmed the structure of the expected polymer as represented in scheme (15).

III—Examples 11 to 13: Syntheses of polyurethanes Starting with the Unsaturated polyolefins of Examples 10, 3 and 8, Respectively

Comparative Example 11: Synthesis of a polyurethane Starting with the Solid Unsaturated polyolefin of Comparative Example 10

The polyolefin of Comparative Example 10 was reacted at 80° C., separately and in a stoichiometric ratio, with a primary diamine of polyetherdiamine type (Jeffamine EDR 148, Huntsman), until complete disappearance of the infrared band characteristic of the 1,3-dioxolan-2-one groups (at 1800 cm⁻¹) and appearance of the bands characteristic of the carbamate bond (band at 1700 cm⁻¹).

The reaction time recorded for complete disappearance of the infrared band characteristic of the 1,3-dioxolan-2-one groups was about 12 hours at 80° C.

Example 12: Synthesis of a polyurethane Starting with the Solid Unsaturated polyolefin of Example 3 According to the Invention Example 11 was reproduced, replacing the polyolefin of Example 10 with the polyolefin of Example 3.

The reaction time recorded for complete disappearance of the infrared band characteristic of the 1,3-dioxolan-2-one groups was less than 3 hours at 80° C.

Example 13: Synthesis of a polyurethane Starting with the Liquid Unsaturated polyolefin of Example 8 According to the Invention Example 11 was reproduced, replacing the polyolefin of Example 3 with the polyolefin of Example 8 and performing the reaction at room temperature (23° C.). The reaction time recorded for complete disappearance of the infrared band characteristic of the 1,3-dioxolan-2-one groups was less than 3 hours at 23° C.

In each case, the products of Examples 12 and 13 were able to be formulated in the form of a two-pack mixture with satisfactory adhesive properties.

The invention claimed is:

1. A hydrocarbon-based polymer comprising two exo-vinylene cyclocarbonate end groups, said hydrocarbon-based polymer being of formula (1) below:

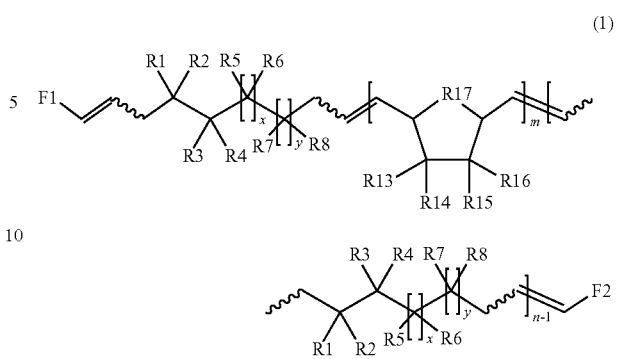

wherein:

each bond noted ⌇ is a carbon-carbon single bond geometrically oriented on one side or the other relative to the double bond to which it is bonded;

the groups R1, R2, R3, R4, R5, R6, R7 and R8, which may be identical or different, are selected from the group consisting of a hydrogen atom, a halogen atom, an alkyl group, a heteroalkyl group, an alkoxycarbonyl group and a heteroalkoxycarbonyl group;

at least one of the groups R1 to R8 optionally forms part of the same saturated or unsaturated hydrocarbon-based ring or heterocycle, with at least one other of the groups R1 to R8;

at least one of the pairs (R1,R2), (R3,R4), (R5,R6) and (R7,R8) optionally is an oxo group;

x and y, which may be identical or different, are integers within a range from 0 to 5;

the groups R13, R14, R15 and R16, which may be identical or different, are selected from the group consisting of a hydrogen atom, a halogen atom, an alkyl group, a heteroalkyl group, an alkoxycarbonyl group and a heteroalkoxycarbonyl group;

at least one of the groups R13 to R16 optionally forms part of the same saturated or unsaturated hydrocarbon-based ring or heterocycle, with at least one other of the groups R13 to R16;

the group R17 comprises $CH_2$, O, S, C(=O) or $NR_0$, $R_0$ being an alkyl group comprising from 1 to 22 carbon atoms; and n comprises an integer greater than or equal to 2 and m comprises an integer greater than or equal to 0, wherein the mole ratio m/n is within a range from 0/100 to 90/10; n and m are also such that the number-average molar mass Mn of the hydrocarbon-based polymer of formula (1) is within a range from 400 to 50 000 g/mol;

F1 is represented by the following formula:

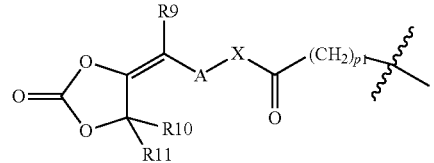

and F2 is represented by the following formula:

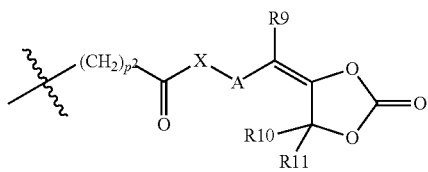

wherein:
p1 and p2, which may be identical or different, each represent an integer equal to 0, 1, 2 or 3;
X is an oxygen atom or a nitrogenous group NR12 in which R12 is a C1-C6 alkyl group;
A is a C1-C6 alkylene group;
R9 comprises a hydrogen atom, a C1-C6 alkyl group, a C1-C6 alkyl group oxyalkylenated with one or more C1-C6 oxyalkylene groups, a C5-C6 cycloalkyl group, a phenyl group or an alkylphenyl group with a C1-C4 alkyl chain; and
R10 and R11, which may be identical or different, each comprise a hydrogen atom, a C1-C6 alkyl group, a C1-C6 alkyl group oxyalkylenated with one or more C1-C6 oxyalkylene groups, a C5-C6 cycloalkyl group, a phenyl group or an alkylphenyl group with a C1-C4 alkyl chain.

2. The hydrocarbon-based polymer comprising two exo-vinylene cyclocarbonate end groups as claimed in claim 1, wherein m is equal to 0, the polymer being of formula (2) below:

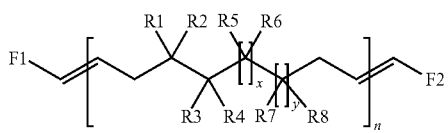

wherein: x, y, n, F1, F2, R1, R2, R3, R4, R5, R6, R7 and R8 are as defined in claim 1.

3. The hydrocarbon-based polymer comprising two exo-vinylene cyclocarbonate end groups as claimed in claim 1, wherein X is an oxygen atom.

4. The hydrocarbon-based polymer comprising two exo-vinylene cyclocarbonate end groups as claimed in claim 1, wherein X is a group NR12 wherein R12 is as defined in claim 1.

5. The hydrocarbon-based polymer comprising two exo-vinylene cyclocarbonate end groups as claimed in claim 1, wherein R12 is a methyl group.

6. The hydrocarbon-based polymer comprising two exo-vinylene cyclocarbonate end groups as claimed in claim 1, wherein R9 is a hydrogen atom, R10 and R11 are methyl groups, and p1=0 or p2=0.

7. The hydrocarbon-based polymer comprising two exo-vinylene cyclocarbonate end groups as claimed in claim 1, wherein p1=p2=0.

8. A process for preparing at least one hydrocarbon-based polymer comprising two exo-vinylene cyclocarbonate end groups as claimed in claim 1, said process comprising at least one step of ring-opening metathesis polymerization, in the presence of:
at least one metathesis catalyst,
at least one mono- or di-exo-vinylene cyclocarbonate chain-transfer agent of formula (C1) or (C2), respectively, below:

wherein:
F1 and F2 are as defined in claim 1, and
the ⁓ bond is a carbon-carbon single bond geometrically oriented on one side or the other relative to the double bond in formula (C2);
at least one compound of formula (A) below:

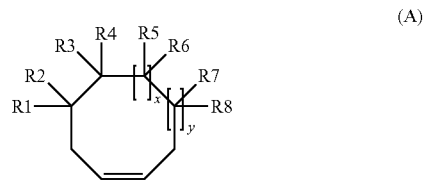

wherein the groups R1, R2, R3, R4, R5, R6, R7 and R8, and x and y are as defined in claim 1; and
optionally, at least one compound of formula (B):

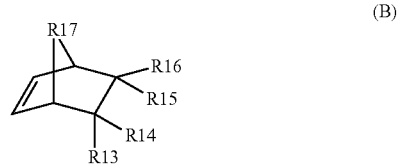

wherein the groups R13, R14, R15 and R16 are as defined in claim 1;
for a reaction time ranging from 2 to 24 hours and at a temperature within a range from 20 to 60° C.

9. The preparation process as claimed in claim 8, said process being such that the mole ratio of the CTA of formula (C1) to the compound of formula (A), or to the sum of the compounds of formulae (A) and (B), if the compound of formula (B) is present, is within a range from $1 \times 10^{-3}$ to 1.0 or the mole ratio of the CTA of formula (2) to the compound of formula (A), or to the sum of the compounds of formulae (A) and (B), if the compound of formula (B) is present, is within a range from $0.5 \times 10^{-3}$ to 0.5.

10. A process for preparing polyurethane, comprising the reaction of at least one hydrocarbon-based polymer of formula (1) as claimed in claim 1 with at least one compound comprising at least one amine group.

* * * * *